United States Patent [19]

Duffett

[11] Patent Number: Plant 5,403

[45] Date of Patent: Feb. 5, 1985

[54] CHRYSANTHEMUM PLANT NAMED RIOT

[75] Inventor: William E. Duffett, Salinas, Calif.

[73] Assignee: Yoder Brothers, Inc., Barberton, Ohio

[21] Appl. No.: 463,923

[22] Filed: Feb. 4, 1983

[51] Int. Cl.[3] ..... A01H 5/00

[52] U.S. Cl. ..... Plt./82

[58] Field of Search ..... Plt./76, 82, 79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Riot having flat capitulum form; decorative capitulum type; red bronze ray floret color; diameter across face of capitulum ranging from 60 to 75 mm. at maturity; uniform nine week photoperiodic flowering response to short days; medium plant height when grown single stem; 10 to 12 cm. peduncles on open, normally terminal sprays; and 13° C. minimum temperature tolerance for initiation and development of flowering buds.

3 Drawing Figures

The present invention comprises a new and distinct cultivar of *Chrysanthemum morifolium,* Ramat., named Riot.

Riot is a product of a planned breeding program which had the objective of creating new chrysanthemum cultivars having low temperature tolerance for cut spray mum programs with decorative capitulum type, bronze ray floret color, nine week flowering response, and the ability to produce commercially acceptable quality in year round programs. Such traits in combination were not present or needed improvement in previously available commercial cultivars.

Riot was originated from a cross made in a controlled breeding program in Salinas, Calif. in 1978. The female parent was identified as 7710010, an unnamed bronze decorative seedling originated from a hybridization of two unnamed seedlings. The male parent of Riot was identified as 772143, an unnamed salmon decorative seedling originated from a cross between (Carillon × Belair) and Delight, all unpatented commercial spray cut mums originated by the present owner.

Riot was discovered and selected as one flowering plant within the progeny of the stated cross by William E. Duffett on June 15, 1979 in a controlled environment in Salinas, Calif.

The first act of asexual reproduction of Riot was accomplished when vegetative cuttings were taken from the initial selection in September 1979 in a controlled environment in Salinas, Calif. by a technician working under formulations established and supervised by William E. Duffett.

Horticultural examination of selected units initiated March 1980 has demonstrated that the combination of characteristics as herein disclosed for Riot are firmly fixed and are retained through successive generations of asexual reproduction.

Riot has not been observed under all possible environmental conditions. The phenotype may vary significantly with variations in environment such as temperature, light intensity, and day length. The following observations, measurements and comparisons describe plants grown in Salinas, Calif. and Leamington, Canada under greenhouse conditions which approximate those generally used in commercial practice.

The following traits have been repeatedly observed and are determined to be basic characteristics of Riot which in combination distinguish this chrysanthemum as a new and distinct cultivar:

(1) Flat capitulum form;

(2) Decorative capitulum type;

(3) Red bronze ray floret color;

(4) Diameter across face of capitulum ranging from 60 to 75 mm. at maturity;

(5) Uniform nine week photoperiodic flowering response to short days;

(6) Medium peduncle length, ranging from 10 to 12 mm.

(7) Medium plant height, requiring 7 to 14 long days prior to short days to attain a flowered plant height of 75 to 90 cm. for May through October flowerings, and (8) Low temperature tolerance of 13° C. (55° F.) for initiation and development when grown in single stem cut spray programs with a continuous dark period of 13 to 14 hours.

The accompanying photographic drawings show typical inflorescence and foliage characteristics of Riot, with the colors being as nearly true as possible with illustrations of this type. Sheet 1 is a color photograph of Riot grown as a single stem cut spray. Sheet 2 is a black and white photograph of three views of the inflorescence of Riot. Sheet 3 is a black and white photograph showing the leaves of Riot at three stages of development (mature, intermediate, immature).

Of the many commercial cultivars known to the present inventor, the most similar in comparison to Riot are Flame Blair, disclosed in U.S. Plant Pat. No. 3,353, and Dark Red Beauregard, an unpatented cultivar. Reference is made to attached Chart A which compares certain characteristics of Flame Belair and Dark Red Beauregard.

Riot has deeper red tonal color than Flame Belair or Dark Red Beauregard. Riot has shorter peduncles than Flame Belair. Riot and Flame Belair are similar in capitulum diameter, with both being larger than Dark Red Beauregard. Both Riot and Flame Belair respond one week earlier than Dark Red Beauregard. Riot has a much superior tolerance of 13° C. for initiation and development of buds than either Flame Blair or Dark Red Beauregard.

In the following description, color references are made to The Royal Horticultural Society Colour Chart. The color values were determined between 1:45 P.M.

and 2:15 P.M. on Aug. 10, 1982 under 150 foot-candle light intensity at Salinas, Calif.

CLASSIFICATION

Botanical: *Chrysanthemum morifolium,* Ramat., cv Riot
Commercial: Spray decorative cut mum.

INFLORESCENCE

Capitulum:
- *Form.*—Flat.
- *Type.*—Decorative.
- *Diameter across face.*—60 To 75 mm.

Corolla of ray florets:
- *Color (general tonality from a distance of three meters).*—Red bronze.
- *Color (abaxial).*—179A.
- *Color (adaxial).*—162B.
- *Shape.*—Narrow. Oblong with pointed tip.

Corolla of disc florets:
- *Color (mature).*—14B.
- *Color (immature).*—1C.

Reproductive organs:
- *Androecium.*—Present disc florets only; very few; scant pollen.
- *Gynoecium.*—Present both ray and disc florets.

PLANT

General appearance:
- *Height.*—Medium; 75 to 90 cm. as a flowering plant from a rooted cutting, with 7 long days for May through October flowerings and maintaining a minimum nightly 13 to 14 hour continuous dark period.

FOLIAGE:
- *Color (abaxial).*—147A.
- *Color (adaxial).*—147B.
- *Shape.*—Deeply lobed and coarsely serrated.

CHART A

COMPARISON OF RIOT AND FLAME BELAIR AND DARK RED BEAUREGARD

| CULTIVAR | RAY FLORET COLOR | CAPITULUM FORM AND TYPE | SPRAY FORMATION |
|---|---|---|---|
| RIOT | RED BRONZE | FLAT DECORATIVE | TERMINAL 10 to 12 cm. PEDUNCLES |
| FLAME BELAIR #3,353 | ORANGE BRONZE | FLAT DECORATIVE | TERMINAL 12 to 15 cm. PEDUNCLES |
| DARK RED BEAU-REGARD | DARK BRONZE | FLAT DECORATIVE | TERMINAL 10 to 12 cm. PEDUNCLES |

| CULTIVAR | DIAMETER ACROSS FACE OF CAPITULUM | PLANT HEIGHT | FLOWERING RESPONSE PERIOD |
|---|---|---|---|
| RIOT | 60 to 75 mm. | MEDIUM 75 to 90 cm. | 9 WEEKS |
| FLAME BELAIR #3,353 | 60 to 75 mm. | TALL 80 to 100 cm. | 9 WEEKS |
| DARK RED BEAU-REGARD | 50 to 60 mm. | MEDIUM 75 to 90 cm. | 10 WEEKS |

COMPARISONS MADE OF PLANTS GROWN AS SINGLE STEM SPRAY CUT MUMS WITH 7 LONG DAYS IN SALINAS, CALIFORNIA

I claim:

1. A new and distinct plant of *Chrysanthemum morifolium,* Ramat., named Riot, as described and illustrated, and particularly characterized as to uniqueness by the combined characteristics of flat capitulum form; decorative capitulum type; red bronze ray floret color; diameter across face of capitulum ranging from 60 to 75 mm. at maturity; uniform nine week flowering response; medium plant height when grown single stem; 10 to 12 cm. peduncles on open, normally terminal sprays, and 13° C. minimum temperature tolerance for initiation and development of flowering buds.

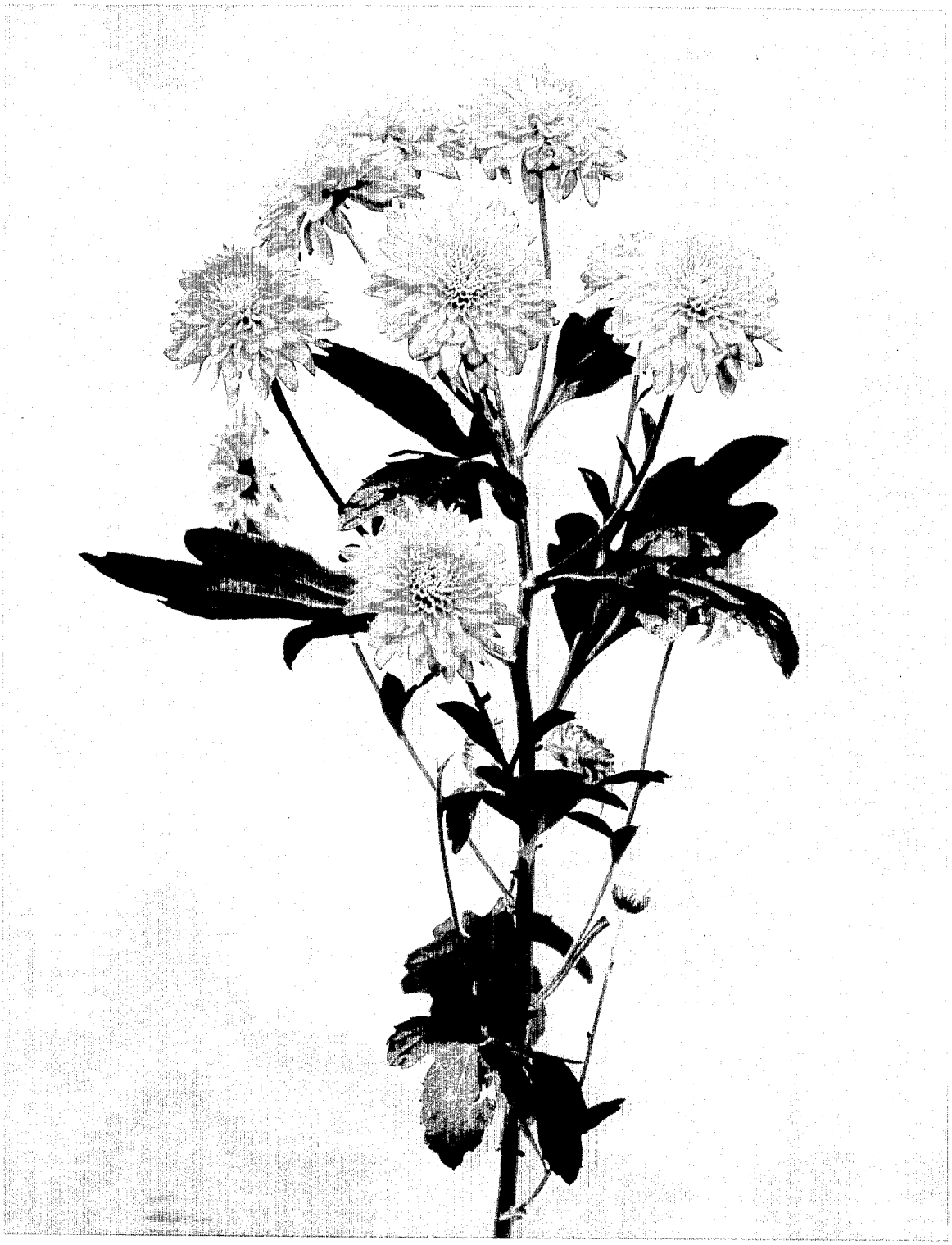

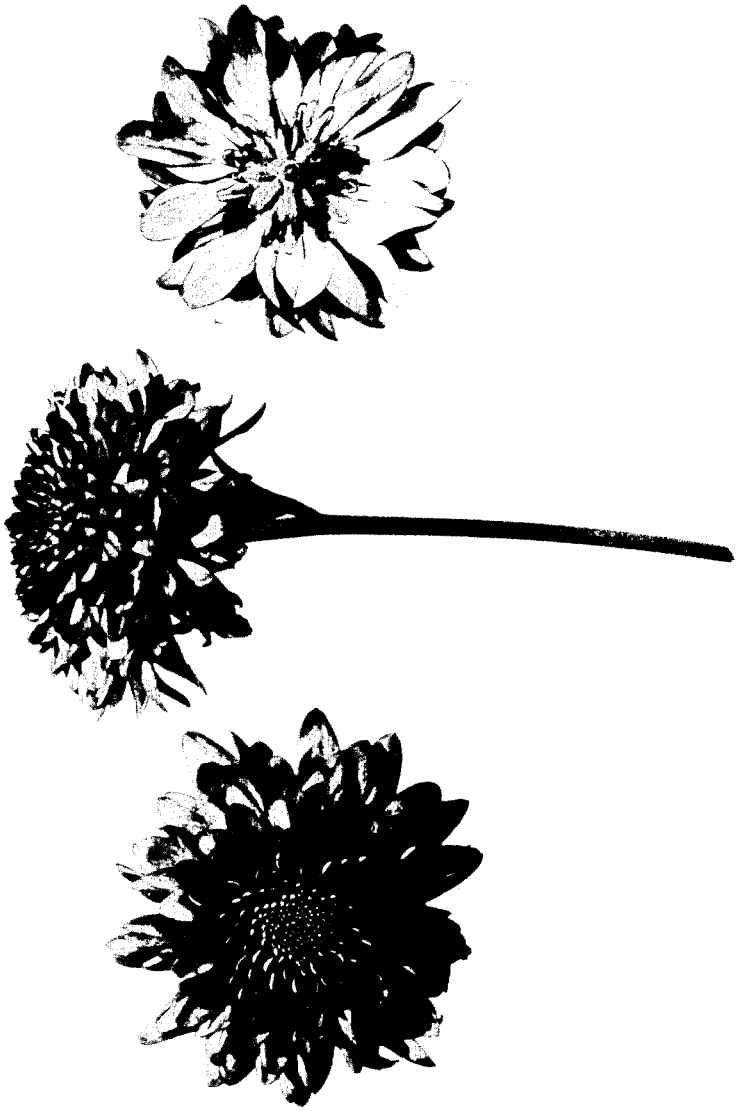

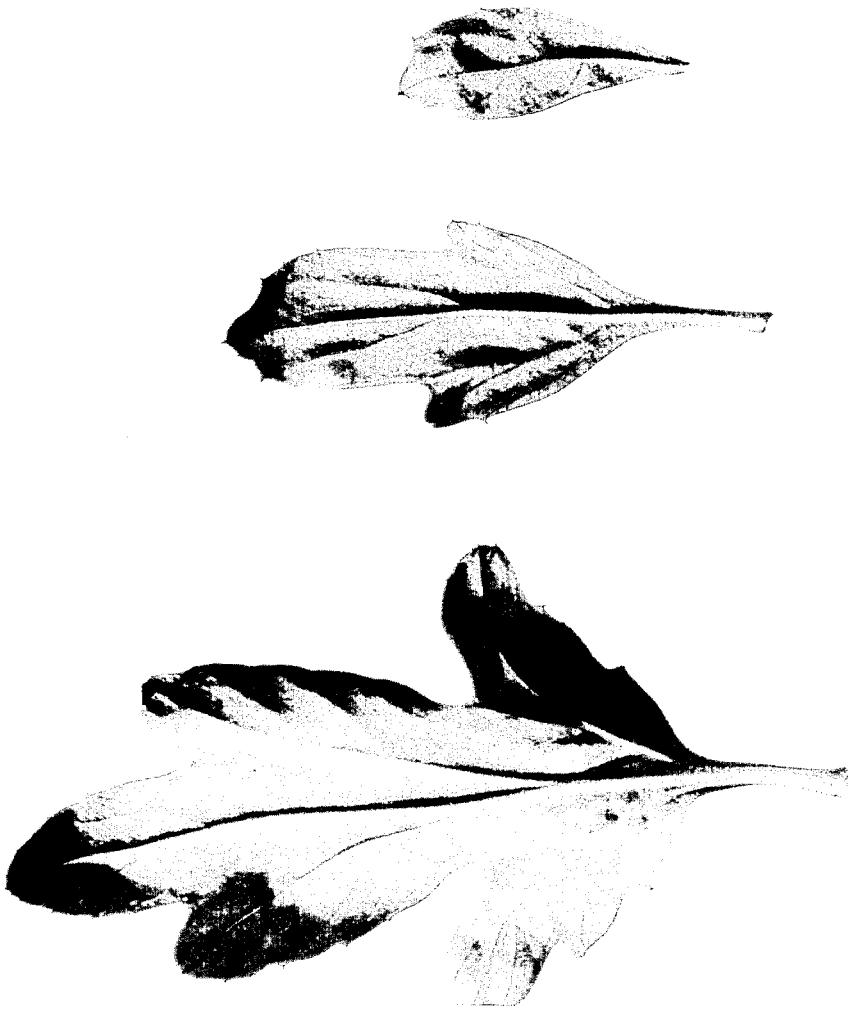

* * * * *